(12) United States Patent
Shirota et al.

(10) Patent No.: US 9,984,847 B2
(45) Date of Patent: May 29, 2018

(54) OPEN-TYPE X-RAY TUBE COMPRISING FIELD EMISSION TYPE ELECTRON GUN AND X-RAY INSPECTION APPARATUS USING THE SAME

(71) Applicant: MARS TOHKEN SOLUTION CO., LTD., Tokyo (JP)

(72) Inventors: Kohei Shirota, Tokyo (JP); Katsunori Minami, Tokyo (JP); Kenji Oohashi, Tokyo (JP)

(73) Assignee: MARS TOHKEN SOLUTION CO., LTD., Tokyo (JP)

( * ) Notice: Subject to any disclaimer, the term of this patent is extended or adjusted under 35 U.S.C. 154(b) by 0 days. days.

(21) Appl. No.: 15/359,946

(22) Filed: Nov. 23, 2016

(65) Prior Publication Data

US 2017/0110283 A1    Apr. 20, 2017

Related U.S. Application Data

(63) Continuation-in-part of application No. 14/197,482, filed on Mar. 5, 2014, now abandoned.

(30) Foreign Application Priority Data

Mar. 15, 2013 (JP) ................................ 2013-053576

(51) Int. Cl.
  *H01J 35/14*    (2006.01)
  *H01J 35/06*    (2006.01)
  (Continued)

(52) U.S. Cl.
  CPC .............. *H01J 35/14* (2013.01); *G01N 23/04* (2013.01); *H01J 35/065* (2013.01); *H01J 35/16* (2013.01);
  (Continued)

(58) Field of Classification Search
  CPC ...... H01J 35/14; H01J 35/16; H01J 2235/087; H01J 35/00; G01N 23/04
  See application file for complete search history.

(56) References Cited

U.S. PATENT DOCUMENTS 4,884,292 A * 11/1989 Klostermann ........ H01J 35/101
  378/127
5,187,371 A    2/1993 Matsui et al.
(Continued)

FOREIGN PATENT DOCUMENTS

JP    37-23305    9/1962
JP    46-022519   8/1971
(Continued)

OTHER PUBLICATIONS

Mars-Tohken X-Ray Inspection Co. Ltd., "Transmission Type X-Ray Inspection Apparatus TUX-3200", [Search: Mar. 12, 2013], Internet < URL: http://www.mars-tohken.co.jp/en/products/xray/detail/id=204 >.
(Continued)

Primary Examiner — Eliza Osenbaugh-Stewart
(74) Attorney, Agent, or Firm — Wenderoth, Lind & Ponack, L.L.P.

(57) ABSTRACT

An object of the present invention is to provide the X-ray tube which improves the workability of the baking for obtaining the ultra-high vacuum of the X-ray tube having a field emission type electron gun and have a stable performance. The X-ray tube comprises a field emission type electron gun chamber, an electron beam aperture, an X-ray target and a vacuum pump, in one body with a vacuum sealing structure (vacuum tube section). The vacuum tube section is attachable and detachable to the electromagnetic lens section in the X-ray tube, thereby it is possible to perform the baking by removing only the vacuum tube section. The fitting portions for positioning are provided at (Continued)

the vacuum tube section and the electromagnetic lens section, and therefore it is a constitution to easily perform an optical axis alignment at a mounting time after the baking.

11 Claims, 8 Drawing Sheets

(51) Int. Cl.
    *H01J 35/16*     (2006.01)
    *H01J 35/30*     (2006.01)
    *G01N 23/04*     (2018.01)

(52) U.S. Cl.
    CPC ......... *H01J 35/30* (2013.01); *H01J 2235/087* (2013.01); *H01J 2235/1204* (2013.01)

(56) References Cited

U.S. PATENT DOCUMENTS

| | | | |
|---|---|---|---|
| 5,629,969 | A | 5/1997 | Koshishiba |
| 5,892,809 | A * | 4/1999 | Wittry ................. G21K 1/06 378/45 |
| 2004/0208280 | A1 | 10/2004 | Yada et al. |
| 2005/0111624 | A1 * | 5/2005 | Yada ................. G21K 7/00 378/136 |
| 2008/0304624 | A1 * | 12/2008 | Aoki ................. H01J 35/08 378/138 |
| 2009/0080617 | A1 * | 3/2009 | Andrews ............... B22D 19/00 378/142 |
| 2010/0040202 | A1 | 2/2010 | Lee |
| 2010/0246766 | A1 * | 9/2010 | Kindlein ............... A61N 5/1001 378/65 |
| 2011/0058655 | A1 | 3/2011 | Okumura et al. |
| 2012/0027177 | A1 | 2/2012 | Ogata et al. |
| 2012/0269323 | A1 | 10/2012 | Adler et al. |
| 2013/0336462 | A1 * | 12/2013 | Suzuki ................. H01J 35/02 378/141 |

FOREIGN PATENT DOCUMENTS

| | | |
|---|---|---|
| JP | 2003-511843 | 3/2003 |
| JP | 2004-138460 | 5/2004 |
| JP | 2004-138461 | 5/2004 |
| JP | 2006-108054 | 4/2006 |
| JP | 2006-294481 | 10/2006 |
| JP | 2008-234981 | 10/2008 |
| JP | 2009-26600 | 2/2009 |
| JP | 2009-301908 | 12/2009 |

OTHER PUBLICATIONS

"Bruker Micro CT SkyScan2011 X-Ray Nanotomograph", [Search: Mar. 12, 2013], Internet < URL: http://www.skyscan.be/products/2011.htm >.

Extended European Search Report dated Aug. 28, 2017 in corresponding European Application No. 14159162.8.

* cited by examiner

PRIOR ART

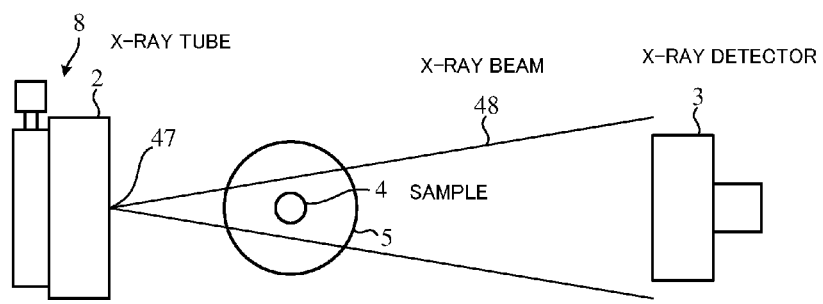
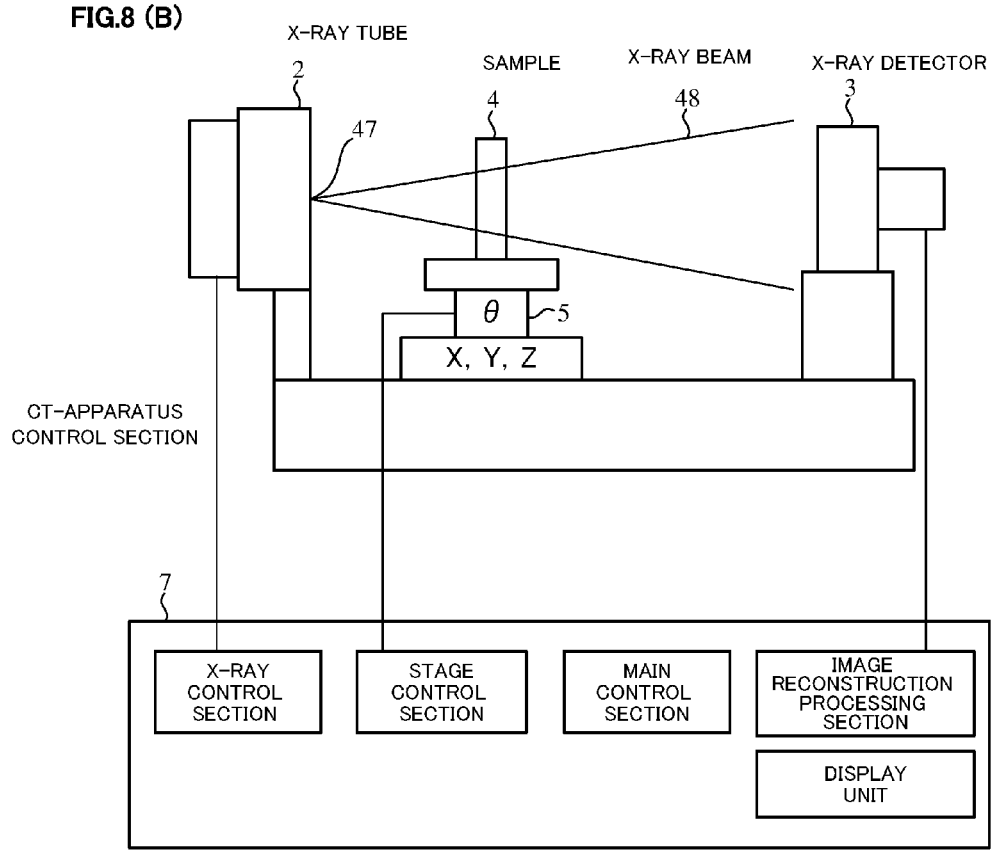

OPEN-TYPE X-RAY TUBE COMPRISING FIELD EMISSION TYPE ELECTRON GUN AND X-RAY INSPECTION APPARATUS USING THE SAME

CROSS-REFERENCE TO RELATED APPLICATION

This is a continuation-in-part of U.S. patent application Ser. No. 14/197,482 filed Mar. 5, 2014.

BACKGROUND OF THE INVENTION

Field of the Invention

The present invention relates to an open-type X-ray tube comprising a field emission type electron gun and an X-ray inspection apparatus using the same, and in particular to a high-resolution type X-ray tube and an X-ray inspection apparatus using the same, whose performances are stable by improving a workability of the baking.

Description of Related Art

With regard to uses of study, development and analytical investigation and so on of biological samples, solid-state materials, industrial electronic parts or the like, inspection apparatuses (hereinafter, merely called "X-ray inspection apparatus(es)"), such as a projection type X-ray inspection apparatus, an X-ray CT apparatus and so on, are known as the apparatuses for observing internal condition and structure of samples at non-destructive and high-resolution. In this high-resolution type (it is operable for the performance to discriminate the sample at a size from few micrometers to a few dozen nanometers.) X-ray inspection apparatus, an X-ray tube having a micro-focus diameter and high-intensity X-ray source is essentially necessary.

The X-ray tube used in such use has an open-type tube constitution. That is, the electron beam emitted from a thermal electron gun (using $LaB_6$ (Lanthanum hexaboride) as the electron source), a field emission type electron gun or a thermal field emission type electron gun (generally called "Schottky-type electron gun(s)") is accelerated with an electrical field, then the electron beam is focused to a beam of extremely micro-focus diameter by using an electron lens, and then the focused beam is irradiated on the X-ray target, thereby to generate the micro-focus diameter and high-intensity X-ray source at the X-ray target. Then, although a sealed type X-ray tube using materials, such as glass and ceramics and so on, for vacuum sealing is generally used, the high-resolution type tube comprising the field emission type electron gun is not put to practical use in the sealed type X-ray tube. That's why it is difficult to maintain the inner of the X-ray tube in ultra-high vacuum condition.

In the projection type X-ray inspection apparatus, a transmission X-ray image is obtained by detecting with an X-ray detector while geometrically enlarging the X-ray image transmitted from the sample by irradiating an X-ray beam generated from the X-ray source to the sample (e.g. refer to Non-Patent Document 1).

In the X-ray CT apparatus, in addition to the above-mentioned constitution, the transmission X-ray images from plural different directions relative to the sample are obtained by rotating the sample relative to the X-ray beam, and then a three-dimensional structural information of the inner of the sample are obtained by generating a set of computed tomographic images due to an image-reconstruction processing of the plural transmission X-ray images. In case of using the X-ray tube that has the X-ray source that a focus diameter is equal to or less than 400 nm, the X-ray CT apparatus having 150-200 nm of the resolution is known (e.g. refer to Non-Patent Document 2).

In order to obtain good X-ray images in the X-ray inspection apparatus, it is necessary to generate a stable X-ray beam by emitting a stable electron beam from the electron source of the X-ray tube. To that end, it is important to keep an ultra-high vacuum condition for a long term by well ultra-highly evacuating ($10^7 \sim 10^{-8}$ Pa) a surrounding area of the electron source of the electron gun. That's why that an emission of electron is unstable, the electron emission characteristic turns down, and the lifetime of the electron source decreases, so gas molecules adsorb on a pointed end portion of the electron source of the field emission type electron gun or the pointed end portion receives an ion bombardment by the gas molecules unless the ultra-high vacuum condition is stable at the surrounding area of the electron source.

In the general art, as shown in FIG. 1, by vacuum-separating a traveling space of an electron beam 103, from an electron gun 100 comprising a Schottky-module 100a, an electron source 100b, an anode 100c, a magnetic-field superposed lens 100d and an electron beam axis alignment coil 100e etc. to an X-ray target 101, from magnetic circuit etc. of an electro magnetic lens (objective lens) 104 prone to gas, it is known to form the surrounding area of the electron source 100b of the electron gun 100 to an ultra-highly vacuum (e.g. refer to Japanese Unexamined Patent Publication No. 2004-138460 A (Patent Document 1)). As well, in FIG. 1, "112" shows an X-ray, the X-ray 112 transmits a sample (object to be inspected), and the transmitted image(s) is/are detected by an X-ray detector 111.

In the open-type X-ray tube, it is well known to use a liner tube (pipe) for the electron traveling path of the electron beam. The liner tube is held by using an elastomer O-ring, which is an airtight sealing member, between an electron gun chamber and a pointed end member including the X-ray target. The airtightness ensures with the above constitution, and the vacuum of the space among the electron gun~the liner tube~the X-ray target is held (e.g. refer to Japanese Unexamined Patent Publication No. 2009-301908 A (Patent Document 2)). Although general electron microscopes also have similar constitutions, the liner tube of the open-type electron tube has an easily detachable constitution in a single body from the main body of the apparatus and is able to carry out the periodical cleaning of the inner wall or the like of the liner tube.

In the X-ray inspection apparatus having the open-type X-ray tube, it is necessary to put the inner of the electron gun chamber in air in the works, such as manufacturing and assembling of the apparatus, change of the electron source nearly and routinely implemented, maintenance of the inner of the electron gun chamber, and so on. Once, to return the electron gun chamber put in air to the ultra-high vacuum condition, the work to make the X-ray tube baking again is necessary. The baking means the work to release the various gas molecules, which are adsorbed or absorbed in a metal surface or inner of a member facing the vacuum of the electron tube apparatus, from the metal surface. By sufficiently baking out before using the apparatus, it is easily operable to evacuate to the ultra-high vacuum condition in a use time. Because it uselessly takes a long time to evacuate unless the baking is sufficient, the required ultra-high vacuum condition is not quite obtained.

It is an ideal that the work of baking is usually performed by heating the member facing the vacuum with a high temperature (200~450° C.) and continuously evacuating for long times (about 24~100 hours) by the vacuum pump (an ion pump, a turbo-molecular pump and so on) for the ultra-high vacuum. As the heating method, for example, it is to continuously evacuate for long times (about 24~100 hours) by the vacuum pump for the ultra-high vacuum, while winding a sheath heater across the apparatus part around the X-ray tube and heating the X-ray tube with a high temperature (200~450° C.) by turning on electricity to the sheath heater. By this baking, it is possible to obtain a stable and ultra-high vacuum tube section including the electron gun chamber.

The electron microscope and so on have constitutions to be able to easily vacuum-separate the electron gun chamber from an electron lens system, the sample chamber and so on. That is, it is operable to bake the only part of the electron gun chamber by using a constitution that an intermediate chamber is provided between the electron gun chamber and the electron lens system and each part is separately evacuated with a differential pumping. In this connection, the method to use the lens system thereafter in usual vacuum ($10^{-3}$~$10^{-4}$ Pa), while only keeping the part of the electron gun chamber in the ultra-high vacuum ($10^{-7}$~$10^{-8}$ Pa), is also much used.

On the contrary, since the X-ray inspection apparatus has the constitution which is difficult to perform the vacuum-separation by such the differential pumping, the method to entirely bake with the inclusion of the electron lens system is adopted.

As the constitution for easily performing the baking of the electron microscope, it is proposed to vacuously separate the electron gun chamber from the liner tube and so on by providing a gun valve on an exit of a field emission type electron gun chamber and closing the gun valve. It is operable to individually bake the only surrounding portion of the electron gun chamber by detaching the electron gun chamber from the main body of the electron microscope apparatus while keeping the inner of the electron gun chamber in vacuum (e.g. refer to Japanese Unexamined Patent Publication No. 2006-294481 A (Patent Document 3)).

THE LIST OF PRIOR ART DOCUMENTS

Patent Document

Patent Document 1: Japanese Unexamined Patent Publication No. 2004-138460 A
Patent Document 2: Japanese Unexamined Patent Publication No. 2009-301908 A
Patent Document 3: Japanese Unexamined Patent Publication No. 2006-294481 A Non-Patent Document Non-Patent Document 1: "Bruker Micro CT SkyScan2011 X-ray nanotomograph", [Search: Mar. 12, 2013], INTERNET<URL: http://www.skyscan.be/products/2011.htm>

SUMMARY OF THE INVENTION

As the above-mentioned, since the electron tube using the field emission type electron gun needs the ultra-high vacuum (degree of vacuum: $10^{-7}$~$10^{-8}$ Pa), an evacuating system of the vacuum tube section adopts the constitution combining the ion pump or a getter pump for exclusive to the electron gun chamber in addition to a turbo-molecular pump and so on.

Further, in the high-resolution type X-ray inspection apparatus and so on using an open-type X-ray tube, it is necessary to raise the current amount of the electron beam 2~3 digits greater than that of the electron tube apparatus such as a usual electron microscope, for an advancement of workability and the shortening of the acquired time of the X-ray image. The general electron microscope obtains the signals interacted with the sample by directly irradiating the focused electron beam to the sample. On the other hand, the X-ray inspection apparatus obtains the image signals interacted with an X-ray and the sample by irradiating the X-ray, which is generated by irradiating the focused electron beam to the X-ray target, to the sample. The energy conversion efficiency of the X-ray generating relative to an incident electron beam in the X-ray target is quite-small insomuch as less than 1%, therefore the amount of the obtained signal is correspondingly diminutive. In the X-ray inspection apparatus, it is necessary to obtain the good X-ray images over a short time, because of the request of the advancement of the workability. Thus, with respect to the current amount (the ranges of a few pA to a few hundred nA on the sample surface) of the electron beam usually used in the general electron microscope, in the high-resolution type X-ray microscope apparatus, it is necessary to raise, a few digits, the current amount of the electron beam as a range of a few µA to a few dozen µA on the surface of the X-ray target.

In the X-ray tube, the electron beam collides on the electron optical parts such as a liner tube, an electron beam aperture, an X-ray target and so on. In these collisions, desorption and re-adsorption of the gas molecules take place on the metal surfaces of the electron optical parts. The larger the current amount of the electron beam is, the larger the influences of these gas molecules are. In the X-ray tube belonging to the present technical art, since it is necessary that the current amount of the electron beam of the X-ray tube raises a few digits greater than the current amount used in the general electron microscope and son on, it is not easy to avoid the influence of the emitted gas due to these strong electron beams. In order to generate a stable X-ray, it is potently desired to preferably suppress the increase of vacuum level in use of the X-ray tube by fully causing the release of the gas molecules including in the surface or inner of the metal. This is especially important in the X-ray inspecting apparatus of which the constitution of the differential pumping is difficult.

In the baking of the general X-ray inspection apparatus, there were the following problems. Since the parts such as an elastomer O-ring, of which the upper operating temperature is low (e.g. 120~150° C.), are included in the X-ray tube, the upper baking temperature is limited by the operating temperature of the above parts, there has been a problem that it is impossible to heat to a high temperature exceeding 200° C. for a long time and perform the enough baking. Further, since the members (e.g. an electron magnetic lens having a large heat capacity located around the vacuum tube section, a column, peripheral members of the apparatus, and so on) which do not need to essentially perform the baking are thermally connected with the X-ray tube, it could not help but integrally heating. For this reason, a large energy for heating was necessary, while the usage efficiency of the energy was low. Moreover, in parallel, it was a problem that the necessary time for heating was long.

Furthermore, since the baking is performed in the X-ray tube being integrated into the apparatus, in a part of the vacuum tube section of the X-ray tube, for example the part that the pointed end portions of the liner tube are intricately integrated into the peripheral parts, a direct heating is not easy and temperature unevenness partially occurs. For this reason, the inner members of the vacuum tube section could not be heated on uniform temperature. As a result, there was a problem that a uniformly-stable baking could not be performed and it was difficult to obtain the good long-stable ultra-high vacuum in the open-type X-ray tube.

The problem to be solved by the present invention is to solve the above mentioned-problems of the conventional art in the high-resolution type X-ray inspection apparatus using the open-type X-ray tube. Concretely, with regard to the vacuum tube section of the X-ray tube of the X-ray inspection apparatus, the problems are to permit the baking in a high temperature range of 200~450° C. not depending on the temperature limit of the usage parts, to permit the energy-efficient baking, to reduce the time and effort of the baking, and to shorten the necessary time of the baking. Further, the present invention aims to perform the baking by uniformly heating the whole vacuum tube section of X-ray tube without temperature unevenness. That is, the object of the present invention is to provide the open-type X-ray tube and the X-ray inspection apparatus using the same, whose performances are stable by improving a workability of the baking.

Means for Solving the Problem

The present invention relates to an open-type X-ray tube, the above-described object of the present invention is achieved by that comprising: an electron gun chamber having a field-emission type electron gun for generating an electron beam; an electromagnetic lens section for focusing the electron beam; an electron beam aperture for narrowing the electron beam; an X-ray target to emit an X-ray with an irradiation of the electron beam narrowed by the electron beam aperture; a liner tube section connected to the electron gun chamber, the X-ray target being arranged in the liner tube section; and a vacuum pump for evacuating the electron gun chamber to an ultra-high vacuum and for keeping the ultra-high vacuum; wherein the electron gun chamber, the electron beam aperture, the X-ray target, the liner tube section and the vacuum pump constitute a vacuum tube section in one body with vacuum sealing by using a metal seal, and the vacuum tube section is attachable and detachable to the electromagnetic lens section.

The above-described object of the present invention is more effectively achieved that wherein the metal seal is weld, or brazing, or a metal gasket, or a metal O-ring; or wherein an optical axis of the vacuum tube section and an optical axis of the electromagnetic lens section are axially aligned by fitting a first fitting section located at an outer wall of the liner tube section and a second fitting section located at the electromagnetic lens section as well as by fitting a third fitting section located at the electron beam aperture and a fourth fitting section located at an inner wall of the liner tube section; or wherein the liner tube section has a constitution to be capable of dividing into plural members along a length direction of the liner tube section; or wherein the electromagnetic lens section further comprises a scanning coil to scan the electron beam on the X-ray target, and the liner tube section further comprises a backscattered electron detecting section to detect a backscattered electron reflecting on the X-ray target, thereby to be possible to observe a backscattered electron image on a surface of the X-ray target by that the backscattered electron detecting section has a ceramic detecting-terminal supporting member to support a backscattered electron detecting electrode; or wherein there is provided a scattered radiation aperture to block a scattered electron beam and a scattered X-ray generating at the electron beam aperture in the liner tube section; or further including a heat sink structure to cool the X-ray target from out of the ultra-high vacuum; or wherein the electromagnetic lens section is located at a nearest side for the field-emission type electron gun and comprises a first electron lens in which an inside diameter of an upper magnetic polepiece of the first electron lens is larger than an inside diameter of a lower magnetic polepiece of the first electron lens, and the electron gun chamber constitutes a magnetic-field superposed type electron gun by having a convex shape corresponding to a shape of the first electron lens.

Moreover, the present invention relates to the X-ray inspection apparatus, the above-described object of the present invention is achieved by the X-ray inspection apparatus comprising any one of the above open-type X-ray tubes; a sample stage which is irradiated by an X-ray beam from the X-ray tube; and an X-ray detector to detect a transmission X-ray image transmitted to the sample stage.

Effects of the Invention

The vacuum tube section of the open-type X-ray tube according to the present invention has the constitution not having the parts which have temperature limitation (e.g. 120~150° C.), such as an elastomer O-ring and so on, and the constitution being easily capable of picking up from the electron magnetic lens section and being detachable while keeping the ultra-high vacuum. Accordingly, it is possible to uniformly and energy-efficiently perform the baking of the single body of the vacuum tube section without temperature unevenness in a high temperature (e.g. 200~450° C.). Moreover, because of the constitution appropriate to heat in a thermostatic oven, a workability of the baking is also improved. In addition, because the portions except the vacuum tube section may not heat, there is an effect that the range of the part selection broadens while the use of the parts having weakness of heating is possible regard to the above portions.

According to the present invention, since it is adopted the constitution fitting the vacuum tube section with the electron magnetic lens, it is possible to correctly and easily perform an optical axis alignment. As a result, it is possible to improve the workability of the assembly after the baking, and there is an effect that can easily make sure of the reproducibility and stability of the product performance.

According to the present invention, since the change of X-ray target is permitted to replace only the liner tube on a side where the X-ray target is attached and the liner tube on the side of the electron gun is reusable, there are effects of no waste for the usage members and they are economically advantageous. Further, so the backscattered electron detecting section is firm and minimized while the supporting members of the backscattered electron detecting electrodes are made from ceramic materials, it is possible to minimize the pointed end portion of the liner tube for containing the target and the backscattered electron detecting section. As a result, the polepiece radius of the electron magnetic lens section contained the pointed end portion of the liner tube becomes small, the electron magnetic lens can also minimize, and accordingly there is an effect of energy saving that the lens current is also small as well as the lens aberration is suppressed small.

Furthermore, according to the present invention, because of the constitution being able to achieve the compact high-performing magnetic-field superposed type electron gun, there is an effect of the advancement of the performance. Moreover, the X-ray inspection apparatus comprising the open-type X-ray tube of the present invention has a superior effect for a maintenance performance since the X-ray inspection apparatus can easily interchange with one body the vacuum tube section including the electron source being consumption articles, the electron beam aperture, the scattered radiation aperture and the X-ray target. Furthermore, by the open-type X-ray tube having the stable X-ray source at an ultra-high vacuum ($10^{-7}$~$10^{-8}$ Pa), it is possible to provide the X-ray inspection apparatus having the stable performance in the X-ray observation of the sample.

BRIEF DESCRIPTION OF THE DRAWINGS

In the accompanying drawings:

FIGS. 8(A) and 8(B) are structural diagrams showing embodiments of an X-ray CT apparatus according to the present invention. FIG. 8(A) is a plane view of the apparatus, and FIG. 8(B) is a front elevation of the apparatus.

DETAILED DESCRIPTION OF THE INVENTION

Figure 1:
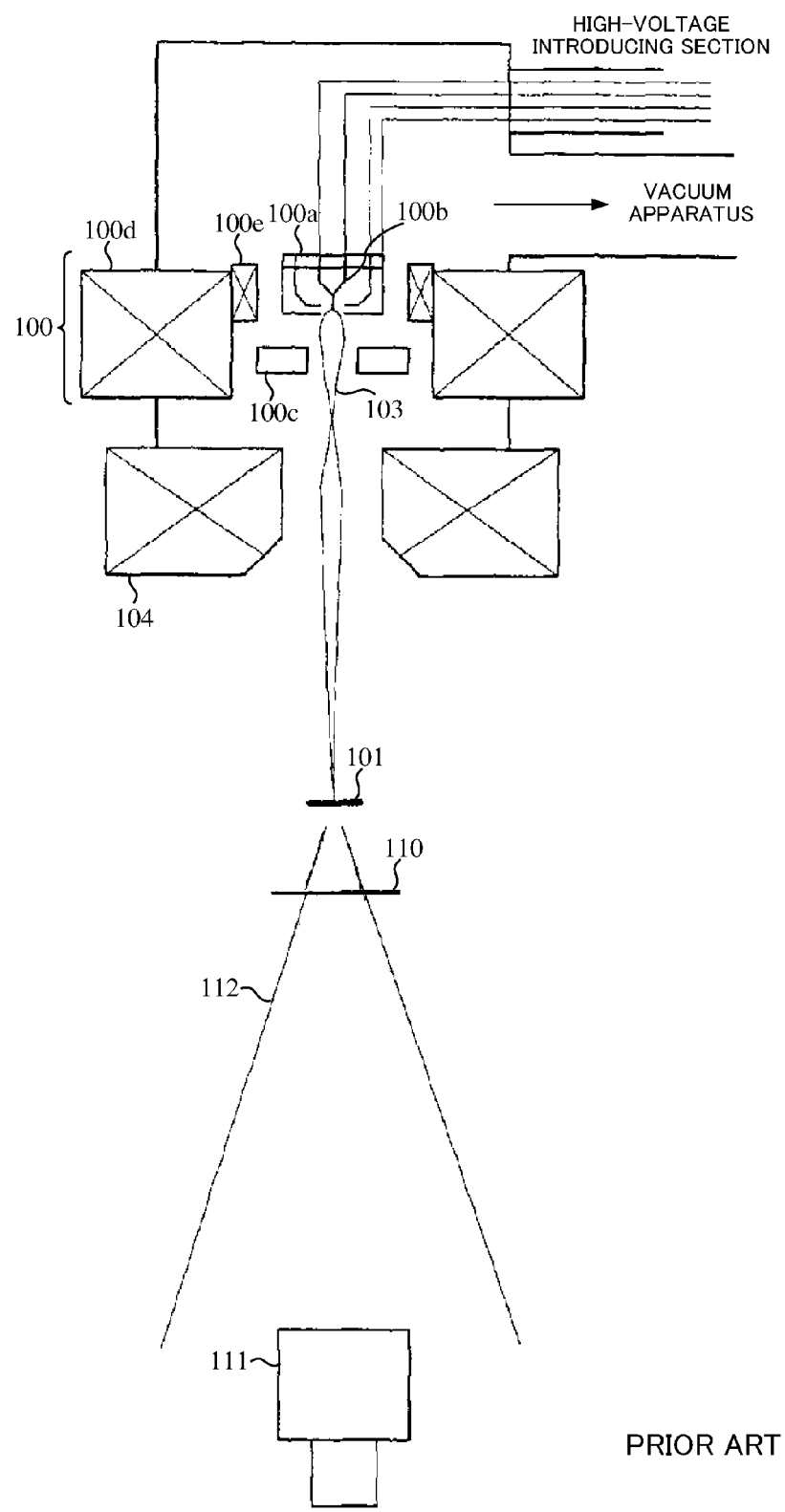
FIG. 1 is a cross-sectional structural diagram showing one example of a structure of a conventional X-ray inspection apparatus.

The X-ray inspection apparatus of the present invention has constitutions explained in the followings for solving the above-described problems. The constitution is what a vacuum tube section is easily detachable from an X-ray inspection apparatus by providing an X-ray tube has a constitution being able to separate the X-ray tube into the vacuum tube section and another sections. The present invention proposes a high-resolution type X-ray tube having a stable performance by improving the workability of the baking and an X-ray inspection apparatus using the X-ray tube.

Hereinafter, embodiments of the present invention will be described in detail with reference to the accompanying drawings.

The present invention relates to an X-ray tube using a field emission type electron source and an X-ray inspection apparatus using the same, and degrees of vacuum to be obtained are ultra-high vacuum ($10^{-7}$~$10^{-8}$ Pa) in an electron gun chamber of the X-ray tube. With regard to expressions of mutual positional relations of parts etc., in case the present description conveniently describes the side of an electron source of an optical axis of an electron optical system as (upper, upper portion, upper end and so on) and describes the side of an X-ray target as (lower, lower portion, lower end and so on), unless specially notice, regardless of a direction of gravity.

A first embodiment of the present invention will be explained with reference to FIG. 2 and FIG. 3.

A main section of an X-ray inspection apparatus 1 of the present invention comprises an X-ray tube 2, a sample stage 5, and an X-ray detector 3. When an X-ray beam 48 generated at an X-ray source 47 in the X-ray tube 2 penetrates a sample 4 of an inspection target held on a sample stage 5, a transmission X-ray image is enlarged to a magnification geometrically defined by an inter-location among the X-ray source 47, the sample 4 and the X-ray detector 3 and then is detected by the X-ray detector 3.

A main section of the X-ray tube 2 comprises a vacuum tube section 11 and an electron magnetic lens section 28. A main section of the vacuum tube section 11 comprises a cylindrically-shaped electron gun chamber 12, a cylindrically-shaped liner tube section 19, an X-ray target 23 downwardly arranged in the liner tube section 19, and a vacuum pump 27 forming and keeping a vacuum condition.

The electron gun chamber 12 mainly comprises an electron gun 13 and an insulator section 14, and the vacuum pump 27 which is connected to an outer of the electron gun chamber 12. A lower end of the electron gun chamber 12 is connected to the liner tube section 19. An electron beam 17 generated from an electron source 16 of the electron gun 13, travels in the liner tube section 19 that is the pathway, receives a focused action from the electromagnetic lens section 28 arranged outside the vacuum around the liner tube section 19, further receives a limitation that a passage of a part of the electron beam 17 is prevented from an electron beam aperture 40, and is then irradiated as an electron probe having an extremely micro-focus diameters on the X-ray target 23. As a result, an X-ray source 47 generating a high-intensity X-ray having a micro-focus diameter is formed on the X-ray target 23. An X-ray component having same direction that is a travelling direction of the electron beam 17 is taken from the X-ray source 47, as an X-ray beam 48 (transmitted target type X-ray beam), in a lower-outer portion of the vacuum tube section 11.

The present invention uses an electron gun 13 of Thermal Field-Emission type (TFE) as the electron source 16 generating the electron beam 17. The electron gun 13 comprises the electron source 16, and two control electrodes (suppressor electrode, extractor electrode) not shown, and these parts are mounted to a nearly-discoidal insulator section 14 (flange made of ceramics) having the diameter about 200 mm. The electron source 16 of the electron gun 13 and the control electrodes are connected to a high-tension cable 15 via some introducing terminals (not shown) passing through the insulator section 14. The insulator section 14 and the introducing terminals have airtight structures with a vacuum sealing. The insulator section 14 is used for the purposes of a vacuum-keeping for an inner of the electron gun chamber 12, the generation of the electron beam 17, and an electric insulation of a necessary high-voltage signal for accelerating. The high-tension cable 15 is connected to an apparatus control section 6 (FIG. 7), as well as, supplies a necessary high-voltage electrical energy for generating the electron beam 17 and an electric control signal to the electron gun 13 through the introducing terminals. As well, the present invention can similarly apply to an electron gun in the case of using a Cold Field-Emission type (CFE).

Figure 2:
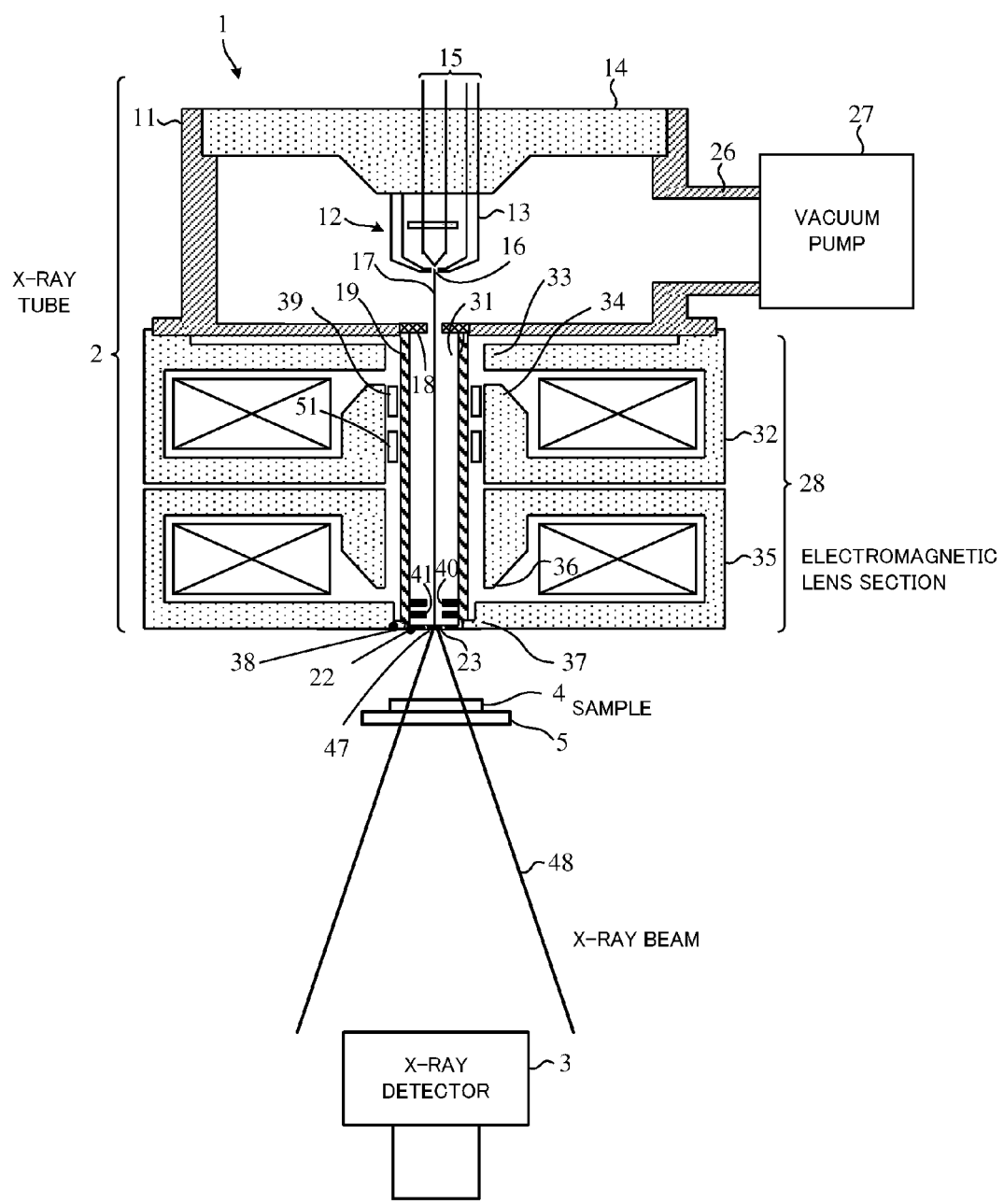
FIG. 2 is a cross-sectional structural diagram showing one example of a structure of an X-ray inspection apparatus according to the present invention.
Figure 3:
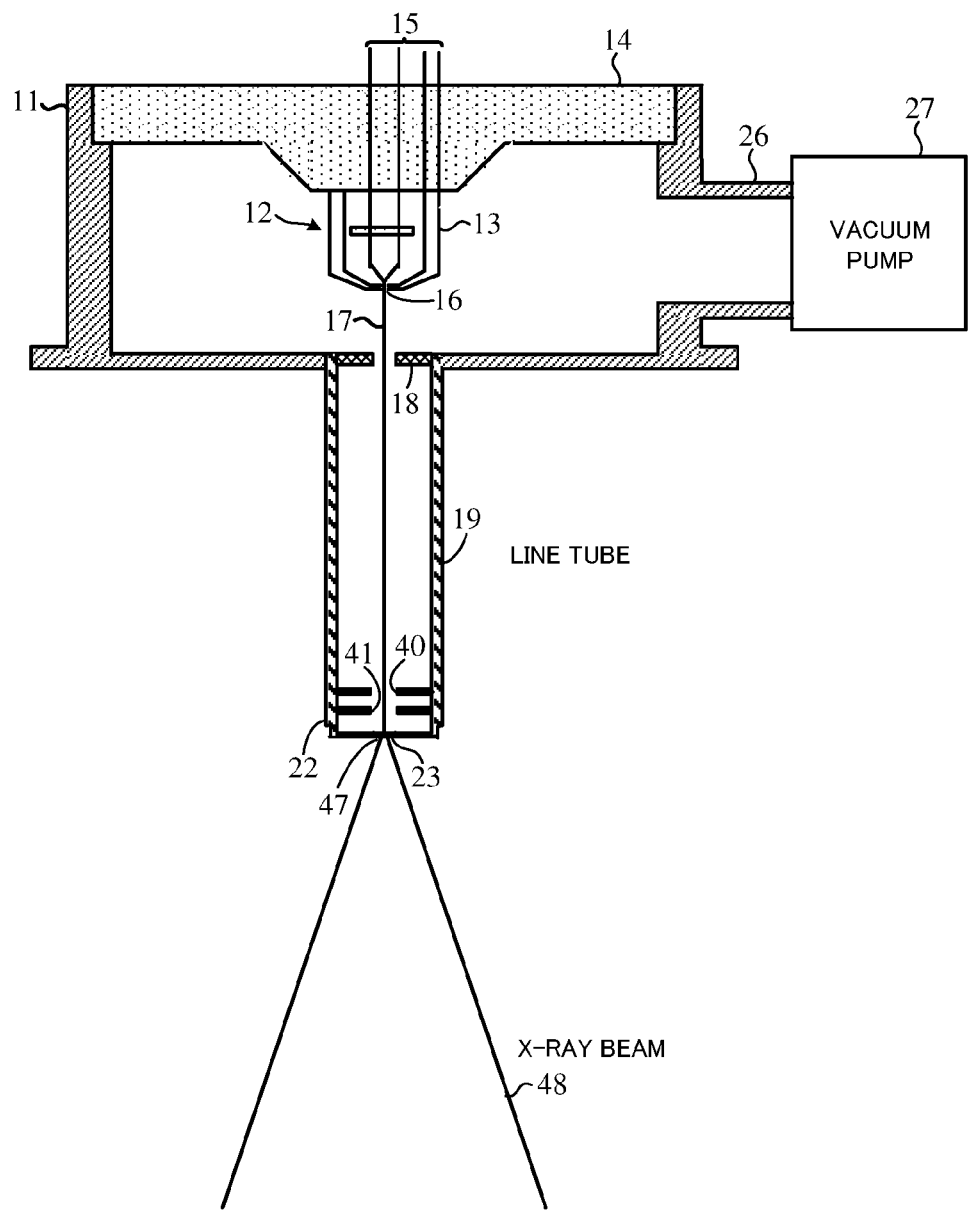
FIG. 3 is a cross-sectional structural diagram showing one example of a structure of a vacuum tube section according to the present invention.

In FIG. 2 and FIG. 3, although only one vacuum port 26 for connecting between the electron gun chamber 12 and the vacuum pump 27 is shown, plural ports may be mounted in a plurality of places in parallel with a vacuum-evacuating system employing. The mounting place and number can be arbitrarily selected.

The vacuum pump 27 for using the apparatus according to the present invention uses by arbitrarily combing a rotary pump or a dry vacuum pump having a large vacuum performance in a low vacuum area, a turbo-molecular pump having a vacuum performance in low to high vacuum areas, an ion pump suitable for keeping ultra-high vacuum etc. with reference to well known methods. Although the electron gun chamber 12 is connected to the ion pump via the vacuum port 26, the constitution placing a non-evaporable getter (NEG) pump may also be further achieved.

While respective members, such as a housing of the electron gun chamber 12, the insulator section 14, the vacuum port 26, the liner tube section 19, the electron beam aperture 40, and the X-ray target 23 and so on, are connected by methods of brazing, weld, or metal seals using a metal gasket or a metal O-ring, an integrally vacuum enclosed space is formed. As well, an elastomer O-ring part for a usual vacuum seal is not used in the present invention. Hereinafter, a section forming the vacuum enclosed space is called "vacuum tube section 11".

The liner tube section 19 (including the X-ray target 23) of the vacuum tube section 11 has a detachable constitution relative to a hole of magnetic polepiece 31 of the electromagnetic lens section 28 (including a scanning coil 39 and a stigmator child 51), and it is possible to draw and take out the vacuum tube section 11 from the X-ray tube 2 at any time. Then, as needed, it is possible to perform the baking and the interchange of the only vacuum tube section 11 in a high temperature by taking out from the X-ray tube while keeping the vacuum of the vacuum tube section 11.

The connection between the electron gun chamber 12 and the insulator section 14 is made by integrating an insulator and a flange by the weld, the brazing, or the metal seals using the metal gasket or the metal O-ring. If vacuum-sealing by the metal seals, by removing the seal of this section, it is possible to change the electron source 16 and the X-ray target 23 by separating the insulator section 14 from the vacuum tube section 11. When changing the electron source 16, the change of the electron source 16 can be easy if removing the metal seal of this section. In this case, the members of the electron gun chamber 12 and the liner tube section 19 can be reused. When changing the X-ray target 23, by removing the metal seal of this section, the change of the X-ray target 23 is to be performed by integrating the electron gun chamber 12 with the exception of the electron gun 13, the liner tube section 19 and the X-ray target 23.

In the present embodiment, a cylindrical section of the electron gun chamber 12 has 205 mm in diameter and 220 mm in height, and a cylindrical section of the liner tube section 19 has 15 mm in diameter and about 85 mm in height. The any mainly materials of them use non-magnetic austenitic stainless steels. Therefore, as shown in FIG. 2 and FIG. 3, the approximate dimension of the whole vacuum tube section 11 has the matter of the dimension which is the cylindrical section of the electron gun chamber 12 plus the cylindrical section of the liner tube section 19. The mass of the vacuum tube section 11 is light-weighted and is about 20~30 kg even if the ion pump, a vacuum valve (not shown) and so on are included. However, the above mentioned values of dimension and mass of the parts are one of embodiment, must not be limited by the values such mentioned, and may be chose appropriate values depending on a purpose of use. Therefore, there are non-conventional effects that the baking with the mounting and removing of the vacuum tube section 11 and the maintenance work can be easily achieved by humans.

The electron gun chamber 12 of the vacuum tube section 11 and the liner tube section 19 of the same are connected by the brazing or the weld. Because of the constitution not to remove the liner tube section 19 from the electron gun chamber 12, the members, such as an elastomer O-ring (the upper endurance temperature is 120~150° C.) and so on, used in a joint portion of the liner tube section 19 of the general electron tube apparatus are not used on the vacuum seal of the vacuum tube section 11. As a result, it is possible to perform the baking of the vacuum tube section 11 in a high temperature. It is possible to easily and uniformly perform the baking of the whole area of the vacuum tube section 11 in a high temperature of a range 200~450° C. Further, since the constitution being able to perform the baking and the interchange of the vacuum tube section 11 alone by releasing the vacuum tube section 11 from the X-ray inspection apparatus 1, the members of the electromagnetic lens section 28 etc. around the vacuum tube section 11 are not thermally influenced. Moreover, so the members (such as electrical wiring member, winding wire material of magnetic field lens, supporting member and so on) except the vacuum tube section 11 has not need of using special heat-resistant members for a baking temperature, it is economical because of being able to use the general member.

FIG. 2 is showing a constitution of the electromagnetic lens section 28, wherein the main section of the electromagnetic lens section 28 comprises a first electron lens (condenser lens) and a second electron lens (objective lens), and wherein the above main section has a function to focus the electron beam 17 generated from the electron gun chamber 12 on the X-ray target 23. A central part of the electromagnetic lens section 28 has a hole of magnetic polepiece 31, and the liner tube section 19 of the vacuum tube section 11 is attachably and detachably arranged in the hole of magnetic polepiece 31. Although the hole of magnetic polepiece 31 is formed by polepieces of the electron lens for determining the lens property, as a matter of convenience herein, the names of the respective polepieces are called, in the order of side from the electron source 16, a first electron lens 32 (a first upper magnetic polepiece 33 and a first lower magnetic polepiece 34) and a second electron lens 35 (a second upper magnetic polepiece 36 and a second lower magnetic polepiece 37). The scanning coil 39 and the stigmator 51 are arranged around the hole of magnetic polepiece 31, and the former has a function scanning the electron beam 17 on the X-ray target 23. The latter has a function correcting an astigmatism of the electron beam.

The X-ray target 23 is integrally placed in a lower end of the liner tube section 19 by the brazing and so on.

In the constitutions shown in FIG. 2 and FIG. 3, when changing the X-ray target 23, it is necessary to exchange by integrating the electron gun chamber 12 except the electron gun 13, the liner tube section 19 and the X-ray target 23 by removing the metal seal of the insulator section 14.

Figure 4:
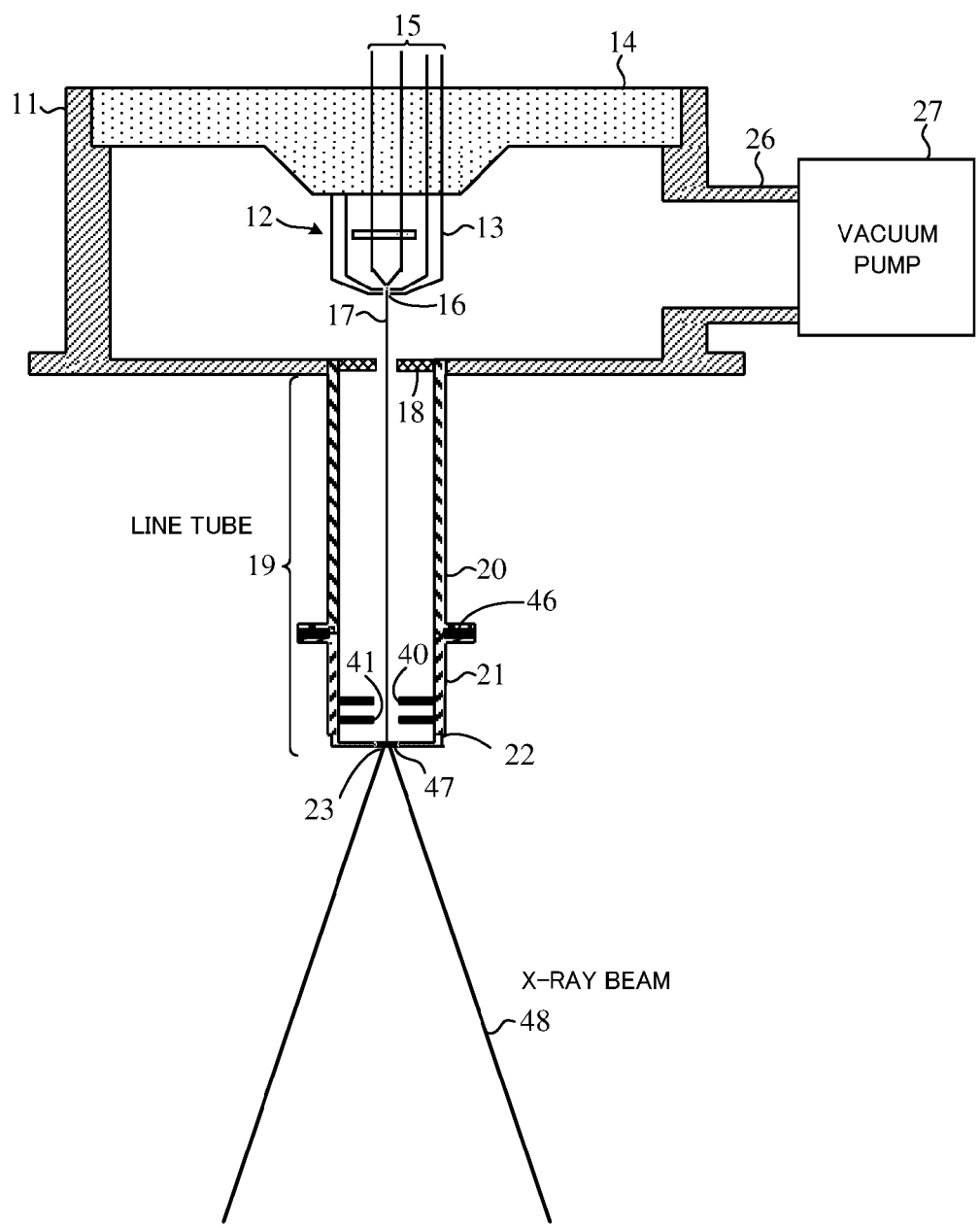
FIG. 4 is a cross-sectional structural diagram showing another example of a vacuum tube section according to the present invention.
Figure 5:
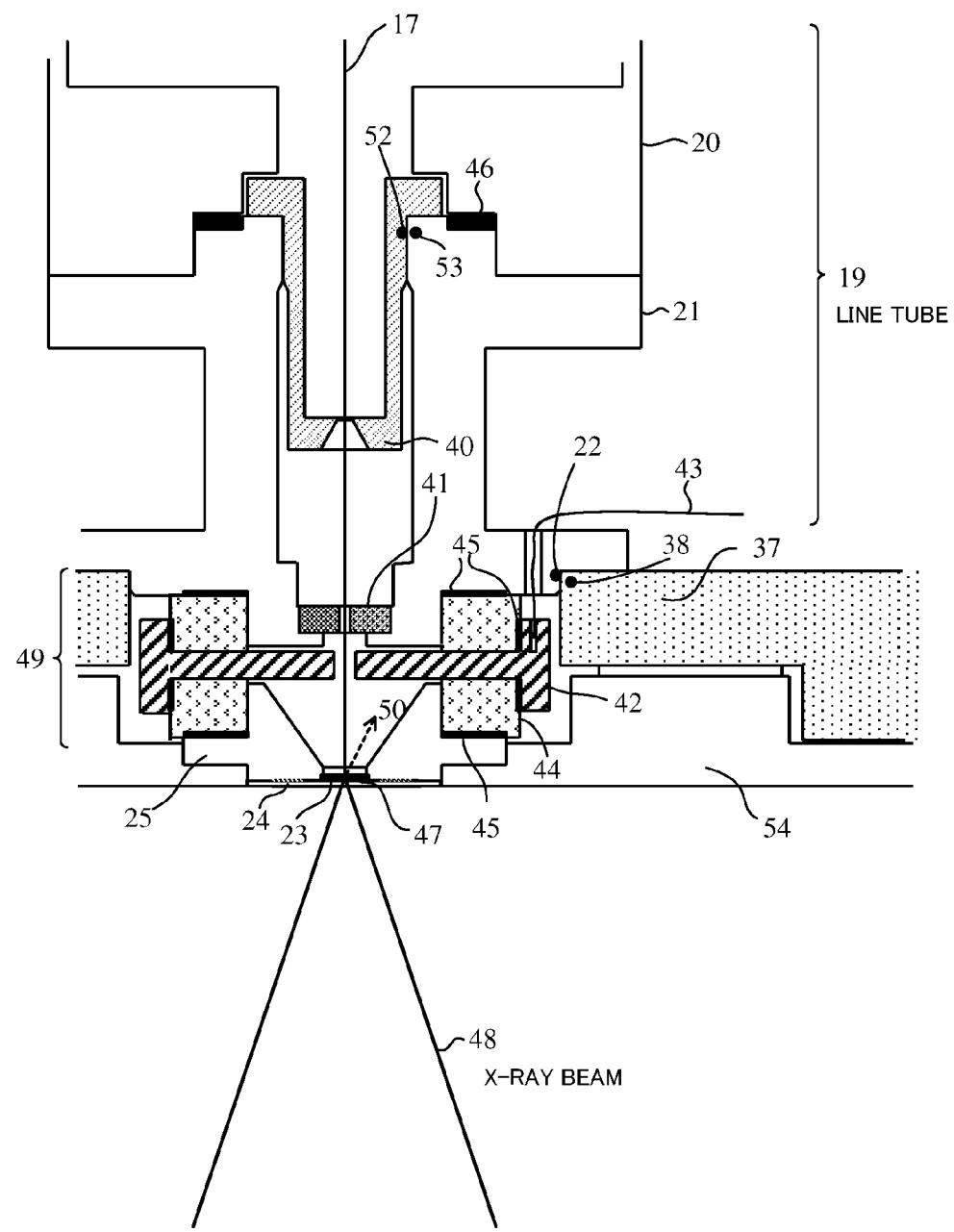
FIG. 5 is a cross-sectional structural diagram showing one example of a structure of a backscattered electron detecting section according to the present invention.

The constitutions for solving these problems are shown in FIG. 4 and FIG. 5. FIG. 4 is showing another constitution example of the vacuum tube section 11, and FIG. 5 is showing one example of a backscattered electron detecting section 49.

With regard to a length direction of the liner tube section 19, the constitution(s) is/are able to divide the liner tube section 19 up and down between an upper liner tube 20 and a lower liner tube 21. Vacuum seals of the divisional ports can use a metal seal such as a metal O-ring 46 or a ConFlat™ flange ("CONFLAT" and "ConFlat" are the trademarks of Agilent Technologies Incorporated.) (or CF flange). The metal O-ring (e.g. "SunLimes™ series" of MITSUBISHI CABLE INDUSTRIES, LTD. "SUNLIMES" and "SunLimes" are the trademarks of MITSUBISHI CABLE INDUSTRIES, LTD.), which is recently commercially-supplied, has about 8 mm in minimum diameter, so the diameter of the metal O-ring is further smaller than that of the ConFlat™ flange, it is possible to minify a size of the divisional port if using the metal O-ring 46. In order to insert or remove the vacuum tube section 11 to or from the X-ray tube 2, although it is necessary to make the diameter of the hole of magnetic polepiece 31 of the electromagnetic lens section 28 larger than an outer diameter of the liner tube 19 in the vacuum tube section 11, the hole can be 15 mm in diameter. By using the present constitution, it is able to exchange the only lower liner tube 21 on the side of having the X-ray target 23. So the members of the electron gun chamber 12 and the upper liner tube 20 can be reused, it is economical because the service parts are reduced. Moreover, the joint port(s) between both liner tubes is/are possible to perform a high-temperature baking because of vacuum-sealing with the metal O-ring 46. As well, instead of the metal O-ring 46, it is possible to use a seal material made of special elastomer, which is possible to bake out in a high-temperature more than 200° C., such as Kalrez™ O-ring ("KALREZ" and "Kalrez" are the trademarks of DU PONT (in US) CO. LTD.) and so on. However, an ultimate pressure deteriorates in comparison with the use of the metal O-ring since Hydrogen and Helium in the air penetrate through the elastomer O-ring.

By using such the metal O-ring 46, since the divisional port of the liner tube section 19 gets smaller, it is possible to arrange a divisional port of the liner tube section 19 near the second lower magnetic polepiece 37 of the second electron lens 35 (refer to FIG. 4 and FIG. 5.). By contrast to the case of using the ConFlat™ flange, it is possible to make the outer diameter of the liner tube section 19 small, and as a result, since it is possible to make small the diameter of the hole of magnetic polepiece 31 of the electromagnetic lens section 28, the electromagnetic lens section 28 itself can also be minimized. Moreover, since an excitation current of the electromagnetic lens section 28 also requires less, a saving of the energy is possible while a calorific power of the electromagnetic lens section 28 also requires less.

An outer diameter of the ConFlat™ flange is 34 mm in the minimum diameter, therefore the large space for mounting is necessary because of using M4-screw for constricting. It is to arrange the ConFlat™ flange within near this upper polepiece by extremely making a diameter of the first upper magnetic polepiece 33 of the first electron lens 32 larger. Although this constitution is not shown, a configuration of the first electron lens is similar shape to the first electron lens 32 shown in FIG. 6 hereinafter.

FIG. 5 shows an example arranging the electron beam aperture 40 that is imperative for focusing of the electron beam 17. A function of the electron beam aperture 40 is to block unnecessary electron beams, such as scattered electron and so on, by controlling an influence of an aberration of the electron lens. In general, it is major to use by making a circular hole in a disk made of a material, such as platinum, molybdenum and so on, having 2-3 mm in outer diameter. A mounting position of the electron beam aperture 40 is major to be in the vicinity of a primary plane of the objective lens having a position which an effect of the aperture is the highest. However, if being able to block unnecessary electron beams and being able to accurately limit a convergence angle of the electron beam 17, it is not very necessary to cling to the material, the shape and the arrangement. It is possible to perform the baking in a high temperature, because the vacuum seals of the mounting portion of the electron beam aperture 40 use the metal O-ring 46.

If the electron beam aperture 40 is eccentrically arranged relative to an optical axis of the electromagnetic lens section 28, since it does not only come up to a huge influence on the aberration, but also the electron beam actively moves when focusing, a huge bad-influence on the performance and the operability is occurred. In this connection, it is absolutely necessary to mechanically position a center of the electron beam aperture 40 with a center of the electromagnetic lens section 28 in high degree of accuracy. Accordingly, first, the thing to do is to accurately position the electron beam aperture 40 on a central axis (on the optical axis) of the liner tube section 19. Next, by accurately positioning the liner tube section 19 of the vacuum tube section 11 in the hole of magnetic polepiece of the electromagnetic lens section 28, it is operable to prevent an eccentricity. Thus, since the centering is performed so that the center of the electron beam aperture 40 is on an optical axis of the electromagnetic lens section 28, it is possible to easily position the both positions of the electromagnetic lens section 28 and the liner tube section 19 by placing the respective fitting sections for fitting on an outer wall of the liner tube section 19 of the vacuum tube section 11 and the second lower magnetic polepiece 37 of the second electron lens 35 and by fitting the fitting sections. That is, a central position of the optical axis, a direction of the optical axis and upper and lower positions of the optical axis direction are easily aligned. Moreover, because the electron beam aperture 40 can be positioned as prescribed relative to the electromagnetic lens section 28, an assembling accurately positioning is possible relative to the optical axis of the electromagnetic lens section 28 and the primary plane of the objective lens.

A constitution of positioning in the divisional type liner tube is shown in FIG. 5, and it is a structure that a fitting section 22 of the lower liner tube 21 is fitted to a fitting section 38 of the second lower magnetic polepiece 37 of the second electron lens 35 and a fitting section 52 of the electron beam aperture 40 is fitted to a fitting section 53 of the lower liner tube 21. By this constitution, it is possible to centering so that the center of the electron beam aperture 40 is on an optical axis of the electromagnetic lens section 28. It is possible to take the vacuum tube section 11 from the hole of magnetic polepiece 31 of the electromagnetic lens section 28 by upward pulling up the liner tube sections (20, 21). In doing so, because the mounting of the vacuum tube section 11 can be accurately and easily, it is possible to make the assembly operation more efficient, as well as easily ensure the repeatability and stability of the product performance. As well, the constitution and effect shown in FIG. 5 are clear to be also able to apply the X-ray tube having the non-divisional liner tube section 19 shown in FIGS. 2 and 3.

FIG. 5 is showing a cross-section of a mainly constitution of a detecting section for observing a backscattered electron image on a surface of the X-ray target 23. As well, the notes of fastener parts, such as screw and so on, are abbreviated. A backscattered electron 50 generated from the surface of the X-ray target 23 is detected on a backscattered electron detecting electrode 42 by scanning the electron beam 17 on the surface of the X-ray target 23 by the scanning coil 39 arranged in the electromagnetic lens section 28. In order to obtain high-resolution type X-ray images, it is necessary to correct an astigmatism of the electron beam 17 by using a stigmator 51 while accurately focusing the electron beam relative to a face of the X-ray target 23. By only observing the X-ray images, it is difficult to do these works. In FIG. 5, the backscattered electron detecting electrode 42 centrally has a hole for giving a passage to the electron beam 17, and has a constitution to efficiently collect the back scattered electron 50 generated from the X-ray target 23 and to take a signal of a backscattered electron 50 on the side of atmosphere with a lead line 43 by placing an opposite arrangement on a position near the X-ray target 23. Moreover, in case of changing the X-ray target 23, the lower liner tube 21 after the metal O-ring 46 and the backscattered electron detecting electrode 42 are integrally changed. With this constitution, it is possible to perform the baking in a high temperature.

A detecting-terminal supporting member 44 shown in FIG. 5 is made of ceramics, and the member has a cylindrical shape. The backscattered electron detecting electrode 42 passes through a side plane of the cylindrical portion of the detecting-terminal supporting member 44 and is vacuum-sealed by the brazing 45 as shown in FIG. 5. Due to this constitution, it is possible to perform the high temperature baking and to satisfy a use in an ultra-high vacuum. When the detecting-terminal supporting member 44 is brazed to the metal, the surface of the brazing is metallized. Because the metallizing process can be optionally performed, at an only necessary part, the process can separate an insulator part and a conductive part. As against a hermetic seal generally used in the detecting section of the scattered electron 50, it is possible to be substantially firm and compact the backscattered electron detecting section 49 by using a supporting member made of ceramics. Because it is possible to minimize a pointed end portion of the liner tube including the X-ray target 23 and the backscattered electron detecting section 49, the outer diameter of the polepiece placing the pointed end portion of the liner tube may be small. Therefore, it is possible to minimize the magnetic field electron lens, and there is an energy saving effect that a lens current may be small while suppressing the lens aberration. As well, the constitution and effect shown in FIG. 5 are clear to be also able to apply the X-ray tube having the non-divisional liner tube section 19 shown in FIGS. 2 and 3.

FIG. 5 is showing a constitution arranging a scattered radiation aperture 41 for blocking backgrounds generated by a scattered electron beam and a scattered X-ray. In the X-ray tube used in the X-ray inspection apparatus, it is difficult to avoid the generation of scattered electron and the scattered X-ray caused by colliding the electron beam 17 against the electron gun 13, the anode 18, the liner tube section 19, and the electron beam aperture 40 and so on. These become backgrounds of the X-ray images by mixing in the primary X-ray beam 48, and then these deteriorate X-ray transmission images. The scattered radiation aperture 41 has a function for reducing the backgrounds by blocking a commingling of the scattered electron and X-ray with the X-ray beam 48. By arranging the scattered radiation aperture 41 backward of the electron beam aperture 40, i.e. at the X-ray target 23 side, a great improvement of the X-ray images is realized. The scattered radiation aperture 41 that is consumable supply is integrally changed with the lower liner tube 21 after the metal O-ring 46, the electron beam aperture 40, the detecting-terminal supporting member 44 (metallization ceramics), the backscattered electron detecting electrode 42, and the X-ray target 23.

FIG. 5 is further showing a constitution cooling the X-ray target 23. The high-resolution type X-ray inspection apparatus 1 uses the X-ray beam 48 outputting from opposite place side of the X-ray target 23, so-called the transmission target type X-ray beam 48, by irradiating the electron beam 17 to the ultra-thin X-ray target 23. Because most energy gets converted to heat when the electron beam 17 having a large energy irradiates to the X-ray target 23, the cooling of the X-ray target 23 is very important. The X-ray target 23 is damaged if the cooling is not enough. The X-ray target 23 is put on a target supporting body 24 having an easily X-ray transparency due to beryllium, diamond or the like and an extremely high thermal conductivity. The heat generated on the X-ray target is radiated to a heat sink 54 which is mechanically contacted to a target holder 25 via the target supporting body 24 and a target holder 25. A constitution of the heat sink 54 variously has forced-air cooling, water cooling, liquid-nitrogen cooling, Peltier cooling and so on. It goes without saying that the constitution of the heat sink of the X-ray target 23 shown in FIG. 5 is practicable in the X-ray tube 2 of the field emission type electron gun of the magnetic-field superposed type shown in FIG. 6.

Next, the baking method will be described. By be composed of an integrated combination of integrating the vacuum pump 27 for ultra-high vacuum, such as an ion pump and so on, with a vacuum port 26 of the vacuum tube section 11, the baking for obtaining ultra-high vacuum is capable by putting the whole integrated combination for a constant time in a high temperature with an evacuation by the vacuum pump 27. A method for making the high temperature condition may heat the only integrated combination of the vacuum tube section 11 detached from the X-ray inspection apparatus 1 and the vacuum pump 27. There is a method heating by looping a sheath heater around the whole integrated combination of the vacuum tube section 11 and the vacuum pump 27. Because of heating not the whole apparatus but the limited part of the only integrated combination of the vacuum tube section 11 and the vacuum pump 27, there is a merit that the mounting of the sheath heater for heating etc. is easy, wherein the vacuum tube section 11 can be uniformly heated without temperature unevenness, and wherein the heating energy can also economize to the minimum necessary.

As another method, by putting the vacuum tube section 11 into the electric furnace, it is also operable to heat the whole with a vacuum. Because the vacuum tube section 11 which is objective to heating is not large, there are also merits that the large electric furnace is no necessary, wherein the uniformly heating without temperature unevenness is operable, wherein the heating energy has no waste, and wherein the temperature control is easy. Further, in any methods, there are merits that the procedure of the heating work is easy and simple, and wherein a work time of the baking can shorten. Other various heating methods are thought. Because of integrally heating and vacuum-evacuating by mounting the vacuum pump 27, such as the ion pump and so on, to the electron gun chamber 12, the method is very effective means as the baking.

Figure 6:
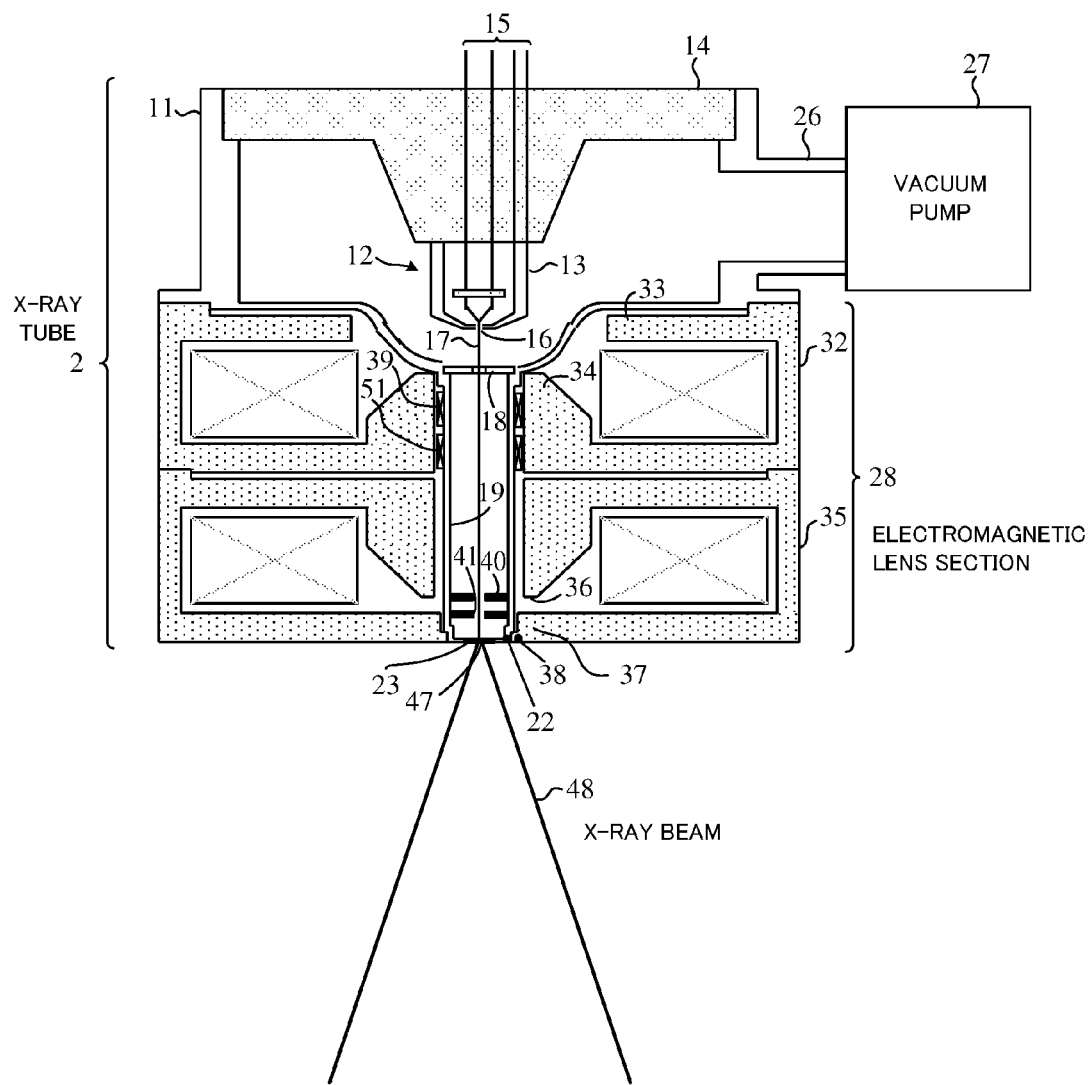
FIG. 6 is a cross-sectional structural diagram showing another example of an X-ray tube according to the present invention.

FIG. 6 is showing other embodiment of the X-ray tube and a constitution for superposing the magnetic field into the internal electric field of the field emission type electron gun 13. In case of using the field emission type electron gun 13 as the X-ray source 47, it is strongly desired to irradiate the large current electron beam 17 to the X-ray target 23 by magnifying the electron source 16 by the electron lens. In this case, it is not operable to irradiate the electron probe having a micro-diameter onto the X-ray target 23, because the general field emission type electron gun widely receives an influence of a spherical aberration coefficient of the first lens (condenser lens). In order to solve this problem, the magnetic-field superposed type electron gun 13 which focuses and accelerates the electron beam 17 by superposing the magnetic field on the electric field in the space between the electron source 16 and the anode 18 before the electron beam 17 from the electron source 16 is spreads, becomes necessary. Thus, it is possible to efficiently use as an electron probe of the electron beam 17 having large electron radiation angle ranges radiated from the electron source 16 and to produce the high-intensity electron probe having a micro-diameter. In the constitution of the present embodiment, in order to arrange the position of the electron source 16 of the electron gun 13 in the magnetic field lens of the first electron lens 32, an inner diameter of the first upper magnetic polepiece 33 of the first electron lens 32 is larger than an inner diameter of the first lower magnetic polepiece 34 of the first electron lens 32, and a bottom face on the side for outputting the electron beam 17 of the electron gun chamber 12 is in such a way as to enter into an altitude of the first lower magnetic polepiece 34 of the first electron lens 32 by taking a convex shape on the downside. In doing so, it is operable to redundantly put the electron field of the electron source 16 of the electron gun 13 on the magnetic field of the first electron lens 32, and the magnetic field superposed type electron gun 13 can be realized.

Figure 7:
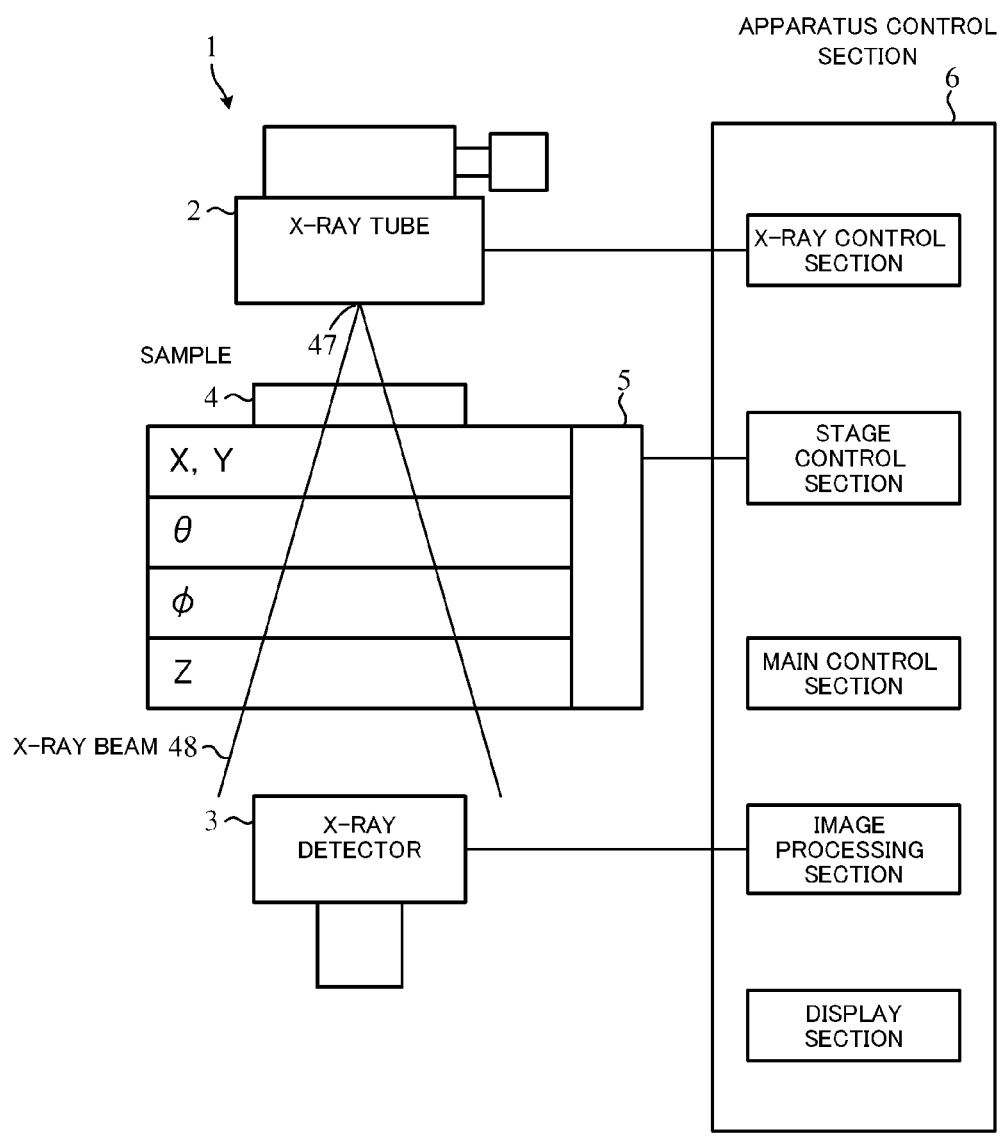
FIG. 7 is a structural diagram showing an embodiment of an X-ray inspection apparatus according to the present invention.

FIG. 7 is showing another embodiment of the present invention. A main section of an X-ray inspection apparatus 1 according to the present invention comprises an X-ray tube 2 of the present invention, a sample stage 5 for placing a sample 4 to be inspected, an X-ray detector 3, and an apparatus control section 6. An X-ray beam 48 generated from an X-ray source 47 of the X-ray tube 2 results in a transmission X-ray image by penetrating the sample 4 to be inspected held on the sample stage 5, the transmission X-ray image is detected by the X-ray detector 3 by being projected and enlarged in a magnification geometrically determined by an inter-arrangement with the X-ray source 47, the sample 4 and the X-ray detector 3. In the high-resolution type X-ray inspection apparatus 1, a position of the sample 4 is imaged in a high magnification by much approximating the X-ray source 47. By relatively moving the sample 4 in regard to the optical axes (the X-ray source 47 to the X-ray detector 3) of an X-ray radioscopy system, the sample stage 5 can set an observing portion and an observing direction. Although the function of the sample stage 5 is well known, five axes relative displacements (three directions of (X, Y, Z) and two rotational directions of (θ, φ)) of the sample 4 is generally often used. The X-ray detector 3 uses flat-panel type semiconductor detector, or image-intensifier type X-ray detector, or a camera for X-ray (refer to Non-Patent Document 1). The apparatus control section 6 comprises a main control section for mainly controlling the operations of the whole apparatus, an X-ray control section for controlling the X-ray tube 2, a stage control section for controlling the sample stage 5, an image processing section for processing an image signal detected by the X-ray detector 3, and a display section for displaying a processed image.

FIG. 8 is showing further other embodiment of the present invention. In FIG. 8 (A), a main section of an X-ray CT apparatus 8 of the present invention comprises an X-ray tube 2 of the present invention, a sample stage 5 for placing a sample 4 to be inspected, an X-ray detector 3, and a CT-apparatus control section 7. An X-ray beam 48 generated from an X-ray source 47 of the X-ray tube 2 results in a transmission X-ray image by penetrating the sample 4 to be inspected held on the sample stage 5, the transmission X-ray image is detected by the X-ray detector 3 by being projected and enlarged in a magnification geometrically determined by an inter-arrangement with the X-ray source 47, the sample 4 and the X-ray detector 3. By relatively moving the sample 4 in regard to the optical axes (the X-ray source 47 to the X-ray detector 3) of an X-ray radioscopy system, the sample stage 5 can set an observing portion and an observing direction. In addition, the sample stage 5 gets transmission X-ray images from a plurality of different directions relative to the sample 4 with a relative rotational-moving to the X-ray beam 48. The X-ray detector 3 uses a flat-panel type semiconductor detector, or an image-intensifier type X-ray detector, or a camera for X-ray. The CT-apparatus control section 7 comprises a main control section for mainly controlling the operations of the whole apparatus, an X-ray control section for controlling the X-ray tube 2, a stage control section for controlling the sample stage 5, an image processing section for reconfiguring and processing by using plural image signals from plural different directions detected by the X-ray detector 3, and a display unit for displaying a processed image. By this constitution, a computed tomography of the sample is generated and then an interior three-dimensional structure information can be obtained (e.g. refer to Non-Patent Document 2). Moreover, the Laminography-type X-ray inspection apparatus using the X-ray tube 2 of the present invention can also obtain a tomographic image of the inner of the sample in the high-resolution.

The X-ray inspection apparatus comprising the X-ray tube of the present invention can easily perform the baking of the X-ray tube and is excellent in the maintenance performance. Moreover, because of using the X-ray tube having the stable X-ray source, the apparatus has stable performances in the observation of the X-ray image of the sample.

As well, the X-ray inspection apparatus of the present invention does not only include the high-resolution and projection type X-ray inspection apparatus, but also the X-ray CT apparatus or generalized X-ray apparatuses using the X-ray tube of the present invention.

What is claimed is:

1. An open-type X-ray tube comprising:
   an electron gun chamber having a field-emission type electron gun for generating an electron beam;
   an electromagnetic lens section for focusing the electron beam;
   an electron beam aperture for narrowing the electron beam;
   an X-ray target to emit an X-ray with an irradiation of the electron beam narrowed by the electron beam aperture;
   a liner tube section connected to the electron gun chamber, the X-ray target being arranged in the liner tube section; and
   a vacuum pump for evacuating the electron gun chamber to an ultra-high vacuum and for maintaining the ultra-high vacuum;
   wherein the electron gun chamber, the electron beam aperture, the X-ray target, the liner tube section and the vacuum pump constitute a vacuum tube section in one body with vacuum sealing by using a metal seal, and the vacuum tube section is attachable and detachable to the electromagnetic lens section,
   wherein the electromagnetic lens section is located at a nearest side for the field-emission type electron gun and includes a first electron lens in which an inside diameter of an upper magnetic polepiece of the first electron lens is larger than an inside diameter of a lower magnetic polepiece of the first electron lens, and the electron gun chamber constitutes a magnetic-field superposed type electron gun by having a convex shape corresponding to a shape of the first electron lens.

2. The open-type X-ray tube according to claim 1, wherein the metal seal is a weld, a brazing, a metal gasket, or a metal O-ring.

3. The open-type X-ray tube according to claim 2, wherein an optical axis of the vacuum tube section and an optical axis of the electromagnetic lens section are axially aligned by fitting a first fitting section located at an outer wall of the liner tube section and a second fitting section located at the electromagnetic lens section as well as by fitting a third fitting section located at the electron beam aperture and a fourth fitting section located at an inner wall of the liner tube section.

4. The open-type X-ray tube according to claim 1, wherein the liner tube section is capable of dividing into plural members along a length direction of the liner tube section.

5. The open-type X-ray tube according to claim 1, wherein the electromagnetic lens section further comprises a scanning coil to scan the electron beam on the X-ray target, and the liner tube section further comprises a backscattered electron detecting section to detect a backscattered electron reflecting on the X-ray target, thereby being possible to observe a backscattered electron image on a surface of the X-ray target, the backscattered electron detecting section having a ceramic detecting-terminal supporting member to support a backscattered electron detecting electrode.

6. The open-type X-ray tube according to claim 5, wherein a scattered radiation aperture is provided to block a scattered electron beam and a scattered X-ray generating at the electron beam aperture in the liner tube section.

7. The open-type X-ray tube according to claim 1 further comprising a heat sink structure to cool the X-ray target from out of the ultra-high vacuum.

8. An X-ray inspection apparatus comprising the open-type X-ray tube described in claim 1; a sample stage which is irradiated by an X-ray beam from the X-ray tube; and an X-ray detector to detect a transmission X-ray image transmitted to the sample stage.

9. An open-type X-ray tube comprising:
an electron gun chamber having a field-emission type electron gun for generating an electron beam;
an electromagnetic lens section for focusing the electron beam;
an electron beam aperture for narrowing the electron beam;
an X-ray target to emit an X-ray with an irradiation of the electron beam narrowed by the electron beam aperture;
a liner tube section connected to the electron gun chamber, the X-ray target being arranged in the liner tube section; and
a vacuum pump for evacuating the electron gun chamber to an ultra-high vacuum and for keeping the ultra-high vacuum;
wherein the electron gun chamber, the electron beam aperture, the X-ray target, the liner tube section and the vacuum pump constitute a vacuum tube section in one body with vacuum sealing by using a metal seal, and the vacuum tube section is attachable and detachable to the electromagnetic lens section,
an optical axis of the vacuum tube section and an optical axis of the electromagnetic lens section are axially aligned by fitting a first fitting section located at an outer wall of the liner tube section and a second fitting section located at the electromagnetic lens section as well as by fitting a third fitting section located at the electron beam aperture and a fourth fitting section located at an inner wall of the liner tube section, and
the electromagnetic lens section is located at a nearest side for the field-emission type electron gun and includes a first electron lens in which an inside diameter of an upper magnetic polepiece of the first electron lens is larger than an inside diameter of a lower magnetic polepiece of the first electron lens, and the electron gun chamber constitutes a magnetic-field superposed type electron gun by having a convex shape corresponding to a shape of the first electron lens.

10. The open-type X-ray tube according to claim 9, wherein the liner tube section is capable of dividing into plural members along a length direction of the liner tube section.

11. An X-ray inspection apparatus comprising the open-type X-ray tube described in claim 9; a sample stage which is irradiated by an X-ray beam from the X-ray tube; and an X-ray detector to detect a transmission X-ray image transmitted to the sample stage.

* * * * *